United States Patent [19]
Murata et al.

[11] 4,263,576
[45] Apr. 21, 1981

[54] HUMIDITY SENSITIVE DEVICE

[75] Inventors: Michihiro Murata, Kyoto; Shinsei Okabe, Takatsuki, both of Japan

[73] Assignee: Murata Manufacturing Co., Ltd., Kyoto, Japan

[21] Appl. No.: 52,502

[22] Filed: Jun. 27, 1979

[30] Foreign Application Priority Data

Jul. 10, 1978 [JP] Japan .................................. 53-84209
Jul. 18, 1978 [JP] Japan .................................. 53-87913

[51] Int. Cl.³ ............................................ H01L 7/00
[52] U.S. Cl. ..................................... 338/35; 252/520; 338/308
[58] Field of Search .......................... 338/35, 308, 309; 252/518, 520; 73/73, 335, 336.5; 340/602; 23/232 E; 422/98; 29/610, 620; 427/101, 102, 372 R, 376 R, 376 B

[56] References Cited

U.S. PATENT DOCUMENTS 4,086,556  4/1978  Nitta et al. ..................... 252/520 X
4,167,725  9/1979  Shimizu et al. ..................... 338/35

FOREIGN PATENT DOCUMENTS 50-98390  8/1975  Japan .

Primary Examiner—C. L. Albritton
Attorney, Agent, or Firm—Ostrolenk, Faber, Gerb & Soffen

[57] ABSTRACT

A humidity sensitive device, including opposing electrodes formed on an insulating substrate, and a humidity sensitive film formed on the surface of the insulating substrate and at least between the opposing electrodes. The humidity sensitive film is obtained by coating on the surface of the insulating substrate a uniformly dispersed mixture including zirconium oxychloride and epoxy resin and heating the same.

35 Claims, 12 Drawing Figures

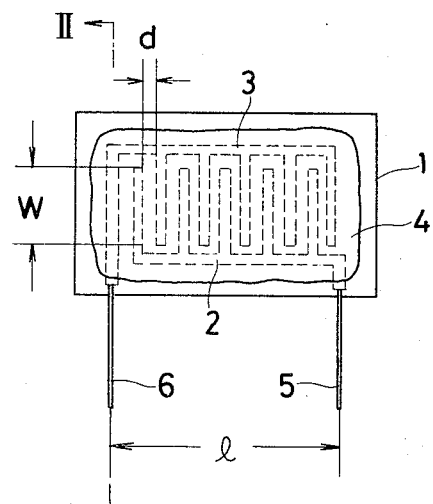
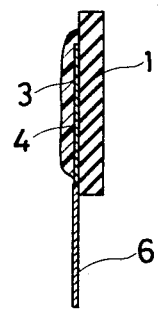
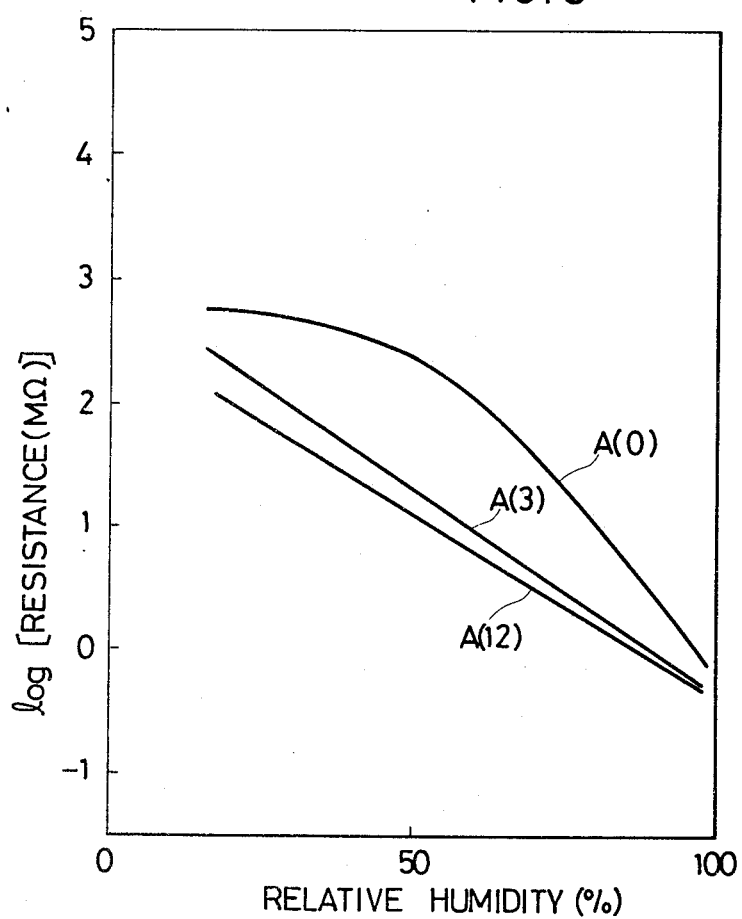

HUMIDITY SENSITIVE DEVICE

BACKGROUND OF THE INVENTION

1. Field of the Invention

The present invention relates to a humidity sensitive device, and more specifically to an improvement in a material composition of a humidity sensitive film.

2. Description of the Prior Art

A humidity sensitive device is typically structured such that opposing electrodes are formed on an insulating substrate and a humidity sensitive film is formed on the surface of the insulating substrate and at least between the opposing electrodes. The humidity sensitive film comprises a material exhibiting a predetermined humidity-resistance value characteristic. Accordingly, the inherent resistance value of the humidity sensitive film is variable as a function of an ambient humidity and as a result a humidity condition can be determined in terms of a resistance value of the humidity sensitive device.

One example of prior art humidity sensitive devices employs an organic high polymer film such as cellulose. However, a disadvantage is encountered in this example that an organic material is liable to be deteriorated during the lapse of time and hence a stabilized characteristic can not be attained.

Another example of prior art humidity sensitive devices employs a metal oxide such as $Fe_2O_3$, $Fe_3O_4$, $Al_2O_3$, $Cr_2O_3$, and the like as a humidity sensitive film. A humidity sensitive film is formed by means of evaporation, sputtering, printing and the like of such metal oxide. It has been observed that a thin film of such metal oxide is superior in absorption property. A variation of humidity is detected in terms of a change of an electrical resistance value by virtue of absorption moisture. An advantage is brought about by such a humidity sensitive film that a response is fast. Nevertheless, a disadvantage is encountered in that a resistance value is relatively high and measurement of a low humidity is rather difficult.

A third typical example of conventional humidity sensitive devices utilizes a ceramic semiconductor. Although a ceramic semiconductor has a feature of excellent heat resisting property, a disadvantage is encountered in that a specific resistivity is high and the cost is expensive as compared with that in case of a humidity sensitive film using an organic resistance film of such material as enumerated in the first example.

SUMMARY OF THE INVENTION

The present invention is aimed to solve the above discussed various problems encountered in the above described conventional humidity sensitive devices.

Briefly described, the present invention comprises a humidity sensitive device, including opposing electrodes formed on an insulating substrate, and a humidity sensitive film formed on the surface of the insulating substrate and at least between the opposing electrodes, wherein the humidity sensitive film is obtained by the steps to be described in the following. More specifically, a uniformly dispersed mixture including zirconium compound and organic polymer is coated on the surface of an insulating substrate and then the same is heated to a temperature that does not decompose the organic polymer. As a result, the zirconium compound serves as a cross linking agent to form a bridge of (-O-Zr-) to the organic polymer and as a result a stable humidity sensitive film is attained. To that end, as the organic polymer, that which has compatibility with zirconium compound is selected.

Thus, a humidity sensitive film thus obtained comprises organic polymer and inoragnic polymer attained by zirconium compound serving as a cross linking agent to the organic polymer.

As described above, zirconium compound is of high reactivity, but in a preferred embodiment, the zirconium oxychloride and zirconium acetate, for example, are used. Besides them, zirconium chloride, zirconium bromide, zirconium hydroxide, zirconium iodide, zirconium nitrate, zirconium oxybromide, zirconium oxyiodide, zirconium sulfate, and the like may also be utilized. Alternatively, compound denatured by hydration of the above described zirconium compounds may also be utilized. As zirconium compound, at least one member is selected from the group of compounds described above.

As organic compound which is compatible with the above described zirconium compound, water soluble polymer (such as ethyl cellulose, metyl cellulose, polyvinyl alcohol and the like), epoxy resin, silicone resin, fluorine-contained polymer and the like are utilized.

In a preferred embodiment of the present invention, at least one member selected from the group consisting of conductive powder, semiconductive powder and insulating powder is doped in the mixture to form a humidity sensitive film. More specifically, such conductive powder, semiconductive powder or insulating powder is aimed to control a resistance value of a humidity sensitive film. More specifically, a resistance value of a humidity sensitive film can be lowered by doping conductive powder, and conversely a resistance value of a humidity sensitive film can be increased by doping insulating powder, while doping of semiconductive powder makes it possible to control a resistance value of a humidity sensitive film in a more delicate manner as compared with the resistance value control by means of conductive powder or insulating powder. Addition of the powder of the above described members serves to increase the surface area of the materials of a humidity sensitive film, thereby to cause the inventive device to exhibit a quick resistance change responsive to moisture. As the above described conductive powder, carbon powder, palladium powder and the like are utilized. As semiconductive powder, the powder of $CrO_2$, $NiO$, $Fe_3O_4$, $ZnO$, $SnO_2$, $MnO_2$, $TiO_{2-x}$ ($0<x<2$), semiconductive alkaline earths titanates such as barium titanate group semiconductor, strontium titanate group semiconductor and the like is utilized. As the insulating powder, the powder of $TiO_2$, $ZrO_2$, $SiO_2$, $Al_2O_3$, and the like is utilized.

Therefore, a principal object of the present invention is to provide a humidity sensitive device, wherein a change of a resistance value due to a humidity variation is increased and thus the sensitivity thereof is enhanced.

Another object of the present invention is to provide a humidity sensitive device, wherein a humidity-resistance characteristic can be adjusted by changing a mixing ratio of the respective materials for the inventive humidity sensitive film.

A further object of the present invention is to provide a humidity sensitive device having a strong humidity sensitive film which deteriorates less with time and of less characteristic variation by virtue of an environmental change.

Still a further object of the present invention is to provide a humidity sensitive device of a quick response rate.

These objects and other objects, features, aspects and advantages of the present invention will be more apparent from the following detailed description when taken in conjunction with the accompanying drawings.

BRIEF DESCRIPTION OF THE DRAWINGS

FIG. 1 is a plan view of one example of a typical humidity sensitive device;

FIG. 2 is a sectional view taken along the line II—II in FIG. 1;

FIG. 3 is a graph showing a relative humidity-resistance characteristics of humidity sensitive devices obtained by Example 1;

DESCRIPTION OF THE PREFERRED EMBODIMENTS

Figure 4:
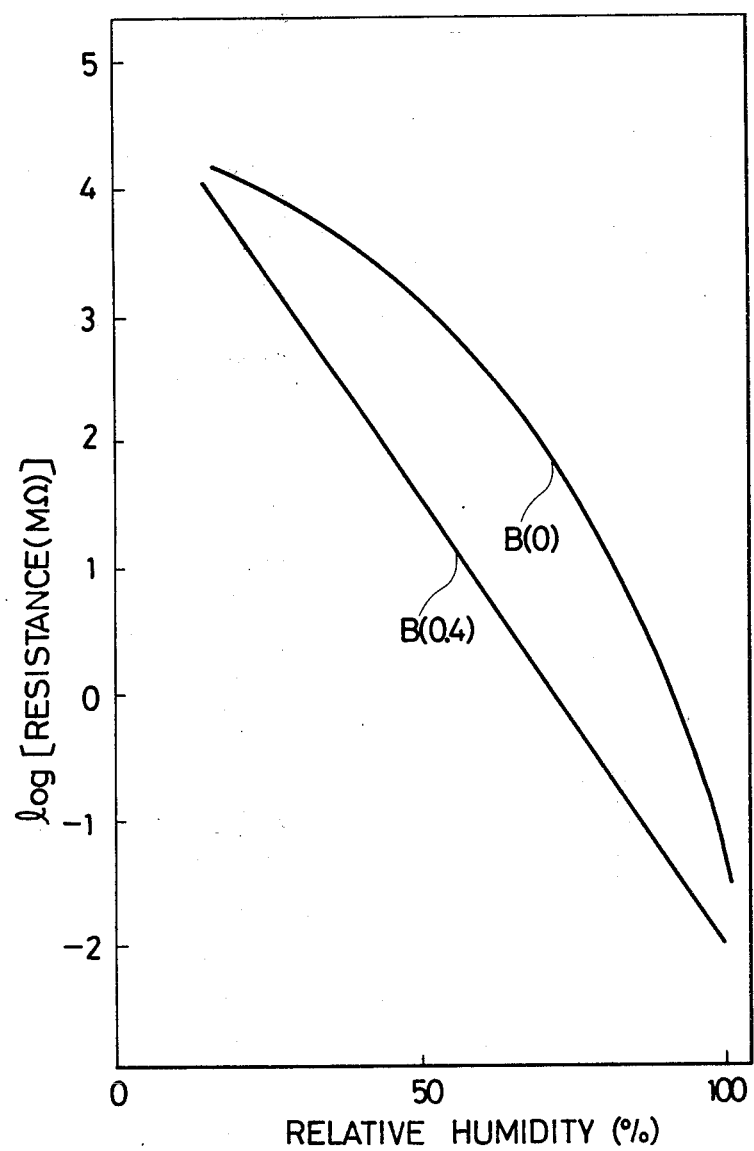
FIG. 4 is a graph showing a relative humidity-resistance characteristics of humidity sensitive devices obtained by Example 2.

FIGS. 1 and 2 show one example of a typical humidity sensitive device. The humidity sensitive device shown comprises an insulating substrate 1 of such a glass, ceramic and the like and opposing electrodes 2 and 3 formed on the insulating substrate 1. The opposing electrodes 2 and 3 are configured in a comb-shape, such that tooth portions thereof are mutually interdigitated or interleaved. A humidity sensitive film 4 is formed on the insulating substrate 1 so as to cover the surface of the insulating substrate where the opposing electrodes 2 and 3 are formed. As a result, the humidity sensitive film 4 is formed on the surface of the insulating substrate 1 and at least between the opposing electrodes 2 and 3. Lead terminals 5 and 6 are electrically connected to the end portions of the respective opposing electrodes 2 and 3 for the purpose of external connection.

An example of a method for forming the above described humidity sensitive film 4 on the insulating substrate 1 will be described. Source materials including zirconium compound and organic polymer are prepared at a predetermind ratio and are mixed and further are mixed with ethyl alcohol, thereby to obtain a paste like uniformly dispersed mixture. The above described paste like uniformly dispersed mixuture is coated on the surface of the insulating substrate 1 where the opposing electrodes 2 and 3 are formed. Then the composite thus obtained is heated and as a result a desired humidity sensitive film 4 is formed on the insulating substrate 1.

In the above described process, after once the source materials are mixed, ethyl alcohol was added to provide a paste like mixture; however, alternatively ethyl alcohol may be added to zirconium compound and then other materials may be added thereby, to obtain a past like mixture.

The inventive humidity sensitive device is characterized by inclusion of inorganic polymer mainly including zirconium obtained by the above described mixing and heating process.

The above described inorganic polymer is attained such that when zirconium compound and organic polymer compatible with the zirconium compound are combined, a bridge of (-O-Zr-) is formed by the zirconium compound as a cross linking agent of the organic polymer, whereupon a portion including the said zirconium becomes an inorganic polymer. The above described bridge of (-O-Zr-) serves to stabilize a structure of the humidity sensitive film. It has been observed that existence in the humidity sensitive film of the inorganic polymer mainly including zirconium not only strengthens the film per se in a solidified state but also largely decreases a resistance value on the occasion of a moisture being absorbed, although the resistance value of the humidity sensitive film in a dry state is very high, and thus considerably increases a variation rate of the resistance value as a function of moisture absorption. Although detailed reasoning of the above described characteristic is not clearly known, it is presumed that electrical conductivity through a cross linkage of (-O-Zr-) largely influences the above described characteristic as a function of moisture absorption. Although a variation of an electrical resistance is observed as a function of moisture absorption even in case of only organic polymer, the resistance value is extremely high even in a moisture absorbed state and no large change of the resistance value is observed, which is a hindrance to practical use of the same. Furthermore, it is extremely difficult to obtain a variety of humidity-resistance characteristics. However, according to a humidity sensitive film employed in the inventive humidity sensitive device, a relatively large variation of a resistance value can be observed even in a low humidity state. In addition, by changing a mixing ratio of zirconium compound, it is possible to change the ratio of the portion forming an inorganic polymer to organic polymer. As a result, by adjusting the ratio of the above described inoraganic polymer, the range of variation of the resistance value can be made large and as a result humidity sensitive devices having any desired humidity-resistance characteristics can be provided. It is intended that by such "any desired humidity-resistance characteristics", a characteristic of approximately a linear resistance value variation with respect to humidity variation, a characteristic exhibiting a large resistance value variation when the humidity exceeds a predetermined value, and the like are covered, for example. The first mentioned linear characteristic is suited for an ordinary humidity sensor, while the second mentioned non-linear characteristic is suited for a dew detector.

In the following the present invention will be further described in accordance with specific examples. It is believed that the present invention is better understood with reference to the following specific examples. However, it should be understood that the following examples are disclosed only for describing the present invention and are not by way of limitation of the present invention.

EXAMPLE 1

Referring to FIG. 1, gold, comb-shaped opposing electrodes 2 and 3 are formed on an insulating substrate 1 made of glass. The dimension concerning the comb-shaped electrodes 2 and 3 is selected such that the total electrode width $l=20$ mm, the electrode distance $d=0.2$ mm, and electrode opposing distance $W=5$ mm.

As materials for the humidity sensitive film 4, 10% polyvinyl alcohol aqueous solutions are prepared, containing 0, 3, and 12% by weight (if in terms of $ZrO_2$) of zirconium oxychloride, respectively. Each of the solutions is coated on the surface of the insulating substrate 1 where the opposing electrodes 2 and 3 are formed and, after drying, the composite is heated at 120° C. for 20 minutes.

A humidity sensitive device thus obtained for each solution is equilibrated in several humidity conditions and thereafter a resistance value is measured. FIG. 3 shows a relative humidity-resistive characteristic obtained by measuring a resistance value of each of the above described humidity sensitive devices at various relative humidities. Referring to FIG. 3, the curve A(0) shows the characteristic of the device containing 0% by weight of zirconium oxychloride, the curve A(3) shows a characteristic of the device containing 3% by weight of zirconium oxychloride, and the curve A(12) shows the characteristic of the device containing 12% by weight of the zirconium oxychloride.

As seen from FIG. 3, the humidity-resistance characteristic of the humidity sensitive device not containing zirconium oxychloride does not exhibit a good proportional relation (see the curve A(0)), but the characteristics of the devices containing zirconium oxychloride exhibit better proportional relations (see curves A(3) and A(12)).

EXAMPLE 2

Those described here are substantially the same as those described in Example 1, except for materials for forming a humidity sensitive film.

As materials for a humidity sensitive film, 2 g of ethylene glycol monobutyl ether solutions containing 20% by weight of ethyl cellulose are prepared and then the same are diluted by adding 1.7 g of ethylene glycol monobutyl ether. An alcohol solution containing zirconium oxychloride is added to the above described solutions such that zirconium oxychloride of the solutions each contain 0 g and 0.4 g of $ZrO_2$, if in terms of $ZrO_2$, whereupon each of the liquids is mixed up to provide a paste like mixture. Each of the paste like mixtures thus obtained is coated on a predetermined area on the surface of the insulating substrate and then the composite is heated at 170° C. for 20 minutes.

The resistance values of the humidity sensitive devices thus obtained are measured at various relative humidities. FIG. 4 shows relative humidity-resistance characteristics thus obtained. Referring to FIG. 4, the curve B(0) shows the characteristic of the device not containing zirconium oxychloride and the curve B(0.4) shows the characteristic of the device containing the above described amount of zirconium oxychloride.

As seen from FIG. 4, as similar to the case of Example 1, the linearity of the characteristic is improved by including zirconium oxychloride.

EXAMPLE 3

The structure of the insulating substrate and the like on which a humidity sensitive film is formed is the same as in case of Example 1.

As materials for a humidity sensitive film, first 0.9 g of epoxy resins of acid anhydride type are prepared. Then an alcohol solution of zirconium oxychloride is added thereto such that zirconium oxychloride in each of the epoxy resins contains 0 g and 0.4 g of $ZrO_2$, if in terms of $ZrO_2$, and each of the same is mixed to provide a paste like mixture. Each of the paste like mixtures is coated on a predetermined surface of the insulating substrate and the composite is heated at 150° C. for 20 minutes.

Figure 5:
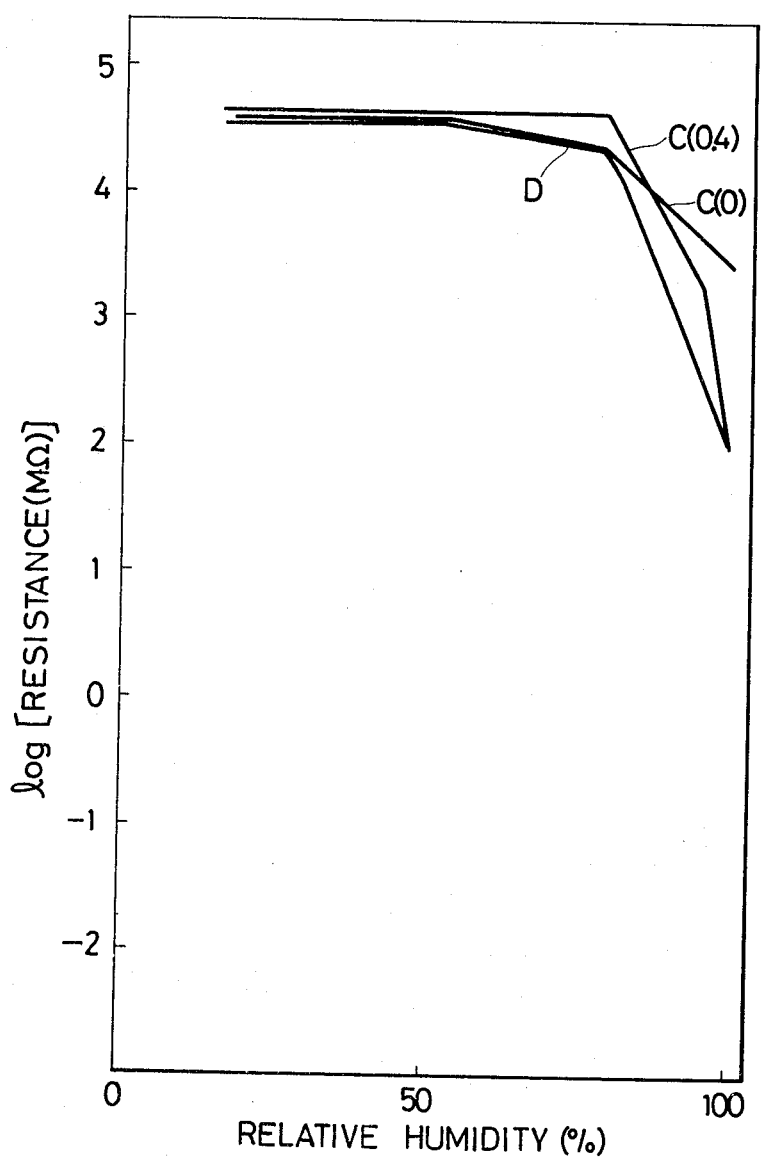
FIG. 5 is a graph showing a relative humidity-resistance characteristics of humidity sensitive devices obtained by Example 3.

The resistance values of the respective humidity sensitive devices thus obtained are measured at several relative humidities. FIG. 5 shows relative humidity-resistance characteristics of the devices thus obtained. Referring to FIG. 5, the curve C(0) shows the characteristic of the device not containing zirconium oxychloride and the curve C(0.4) exhibits the characteristic of the device containing the above described amount of zirconium oxychloride.

Meanwhile, the curve D in FIG. 5 shows the characteristic of a device similarly obtained by substituting zirconium acetate for zirconium oxychloride. In comparison of the curve C(0.4) with the curve D, an appreciable difference is observed therebetween.

As understood from the characteristics of Example 3, the curves C(0.4) and D in FIG. 5 show an abrupt decrease of the resistance value in the vicinity of 100% in terms of the relative humidity. It would be appreciated that this type of characteristic curve is suited for a dew detector. More specifically, these curves show that when much moisture is absorbed by the humidity sensitive film a large resistance value variation is caused.

The above described Examples 1 to 3 substantiate improvements in the characteristics by doping zirconium compound. Several exampls to be described in the following contain at least one member selected from the group consisting of conductive powder, semiconductive powder and insulating powder, as a third material, in addition to zirconium compound and organic polymer, as materials for constituting a humidity sensitive film. Such third component advantageously controls resistance value of a humidity sensitive film.

EXAMPLE 4

Referring to FIG. 2, an insulating substrate 1 is made of alumina and opposing electrodes 2 and 3 made of gold are formed on the insulating substrate. The dimension of the opposing electrodes 2 and 3 are selected such that the total electrode width $l=20$ mm, the electrode distance $d=0.5$ mm, and the electrode opposing distance $W=5$ mm.

As materials for a humidity sensitive film 4, first of all 0.9 g of epoxy resin of acid anhydride type is prepared and 4.7 g of $MnO_2$ powder serving as a semiconductor and 3.8 g of $TiO_2$ powder serving as an insulation are added thereto. An alcoholic solution of zirconium oxychloride (1.8 g of $ZrO_2$, if in terms of $ZrO_2$) is then added and the mixture is mixed and then ethyl alcohol is further added, thereby to provide a paste like mixture of proper viscosity. The paste like mixture is then coated on a predetermined area on the insulating substrate 1 and the composite is heated at the temperature of 150° C.

Figure 6:
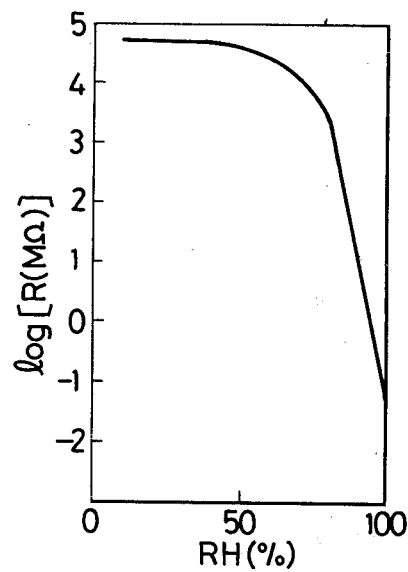
FIG. 6 is a graph showing a relative humidity-resistance characteristic of humidity sensitive device obtained by Example 4.

The resistance values of the humidity sensitive device thus obtained are measured at various relative humidities. FIG. 6 shows a relative humidity-resistance characteristic thus obtained.

EXAMPLE 5

As materials for a humidity sensitive film, 5.2 g of $MnO_2$ powder serving as a semiconductor and 2.3 g of $TiO_2$ powder serving as an insulation are added to 0.9 g of epoxy resin of acid anhydride type. Then an alcoholic solution of zirconium oxychloride (6 g of $ZrO_2$, if in terms of $ZrO_2$) is added thereto and mixed and further ethyl alcohol is added, thereby to provide a paste like mixture of proper viscosity. Then, as in case of the above described Example 4, a humidity sensitive device is fabricated.

Figure 7:
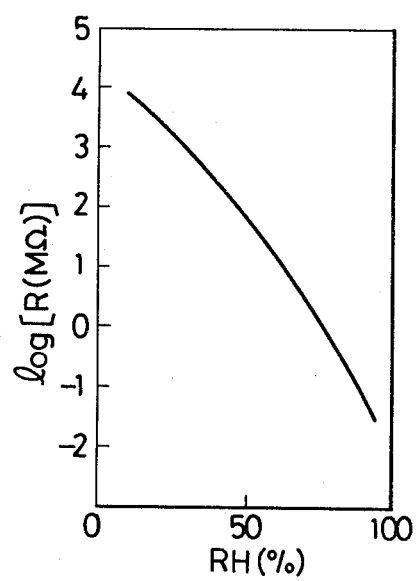
FIG. 7 is a graph showing a relative humidity-resistance characteristic of humidity sensitive device obtained by Example 5.

The resistance values of the humidity sensitive device thus obtained are measured at various relative humidities. FIG. 7 shows a relative humidity-resistance characteristic thus obtained. It is observed that the characteristic shown in FIG. 7 exhibits approximately a linear resistance variation with respect to the relative humidity.

EXAMPLE 6

As the material for a humidity sensitive film, at first 2 g of 16% solution is prepared by solving ethyl cellulose in ethylene glycol monobutyl ether. Then, 1.7 g of $MnO_2$ powder serving as a semiconductor and 1.4 g of $TiO_2$ powder serving as an insulation are added thereto and the mixture is mixed and then an alcoholic solution of zirconium oxychloride (0.16 g of $ZrO_2$, if in terms of $ZrO_2$) is added, thereby to provide a paste like mixture. The paste like mixture is processed in the same manner as in case of Example 4, thereby to provide a humidity sensitive device.

Figure 8:
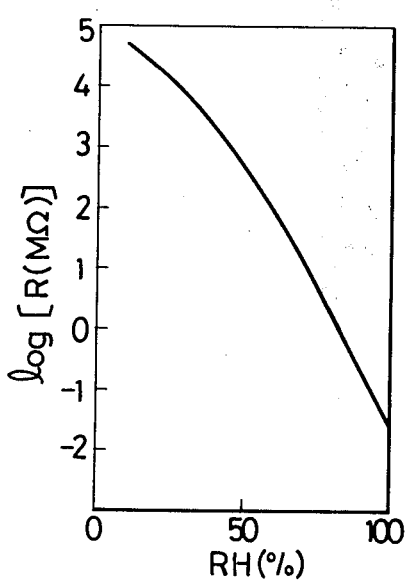
FIG. 8 is a graph showing a relative humidity-resistance characteristic of humidity sensitive device obtained by Example 6.

FIG. 8 shows a relative humidity-resistance characteristic of humidity sensitive device thus obtained.

EXAMPLE 7

In the same condition as in case of Example 6, a humidity sensitive device is fabricated, with zirconium oxychloride, and with 40 mg of $ZrO_2$, if in terms of $ZrO_2$.

Figure 9:
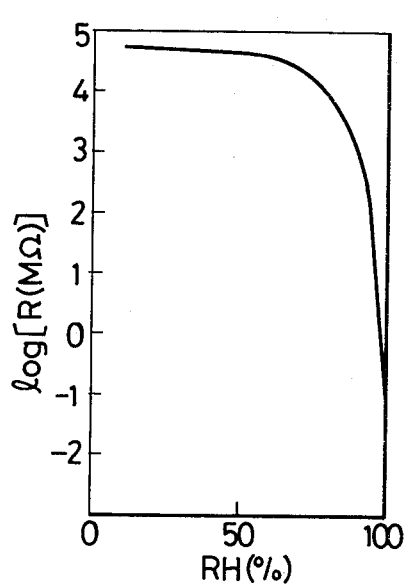
FIG. 9 is a graph showing a relative humidity-resistance characteristic of humidity sensitive device obtained by Example 7.

FIG. 9 shows a relative humidity-resistance characteristic of a humidity sensitive device thus obtained.

EXAMPLE 8

In the same condition as in case of Example 6, a humidity sensitive device is fabricated, using zirconium acetate, with 40 mg of $ZrO_2$ contained, if in terms of $ZrO_2$.

Figure 10:
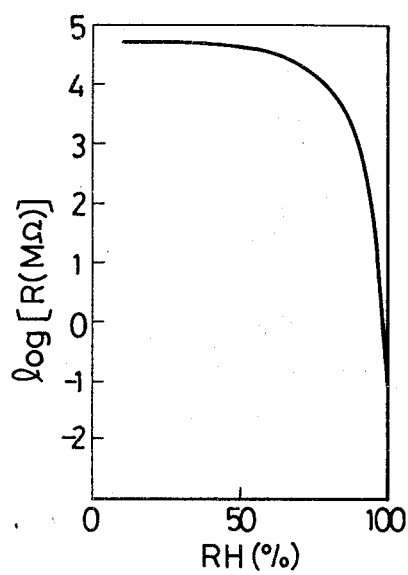
FIG. 10 is a graph showing a relative humidity-resistance characteristic of humidity sensitive device obtained by Example 8.

FIG. 10 shows a relative humidity-resistance characteristic of a humidity sensitive device thus obtained. The characteristic shown in FIG. 10 is substantially the same as shown in FIG. 9.

EXAMPLE 9

As materials for a humidity sensitive film, first 1 g of 10% polyvinyl alcohol aqueous solution is prepared and 31 g of $MnO_2$ and 0.14 g of $TiO_2$ are added thereto. Then zirconium oxychloride (0.018 g of $ZrO_2$, if in terms of $ZrO_2$) and the mixture are mixed to provide a paste like mixture. The paste like mixture thus obtained is processed in the same manner as in case of Example 4, thereby to fabricate a humidity sensitive device. The heating condition is 20 minutes at 120° C.

Figure 11:
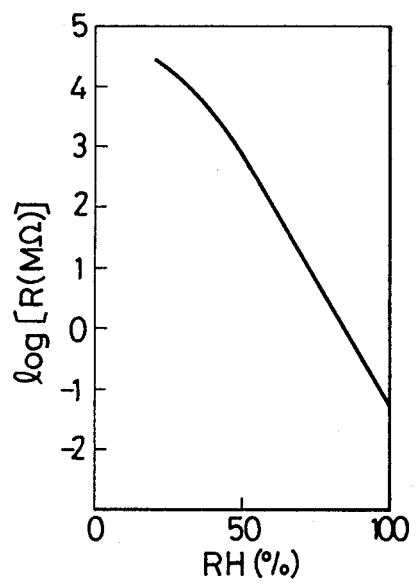
FIG. 11 is a graph showing a relative humidity-resistance characteristic of humidity sensitive device obtained by Example 9.

FIG. 11 shows a relative humidity-resistance characteristic of a humidity sensitive device thus obtained.

The humidity sensitive films of the inventive humidity sensitive devices thus obtained in accordance with the above described various Examples comprise cross linkage of (-O-Zr-). Therefore, the time dependent deterioration of the characteristic is little and the variation of the characteristic by virtue of environmental variation is also little, while a response rate is fast. In order to ascertain small time dependent deterioration of the characteristic of the inventive humidity sensitive device, the following experimentation was made.

A direct current voltage of 12 V is applied to a humidity sensitive device obtained by Example 4. With such a state maintained, the humidity sensitive device is placed in the atmosphere of the temperature of 40° C. and the relative humidity of 95% for 100 days. Then, the humidity sensitive device is returned to a normal condition and then the resistance values of the device at various relative humidities are measured. The relative humidity-resistance characteristic thus obtained is shown by the curve E in FIG. 12. The relative humidity-resistance characteristic as measured with respect to a humidity sensitive device as obtained by the above described Example 4 is also shown by the curve F in FIG. 12.

Figure 12:
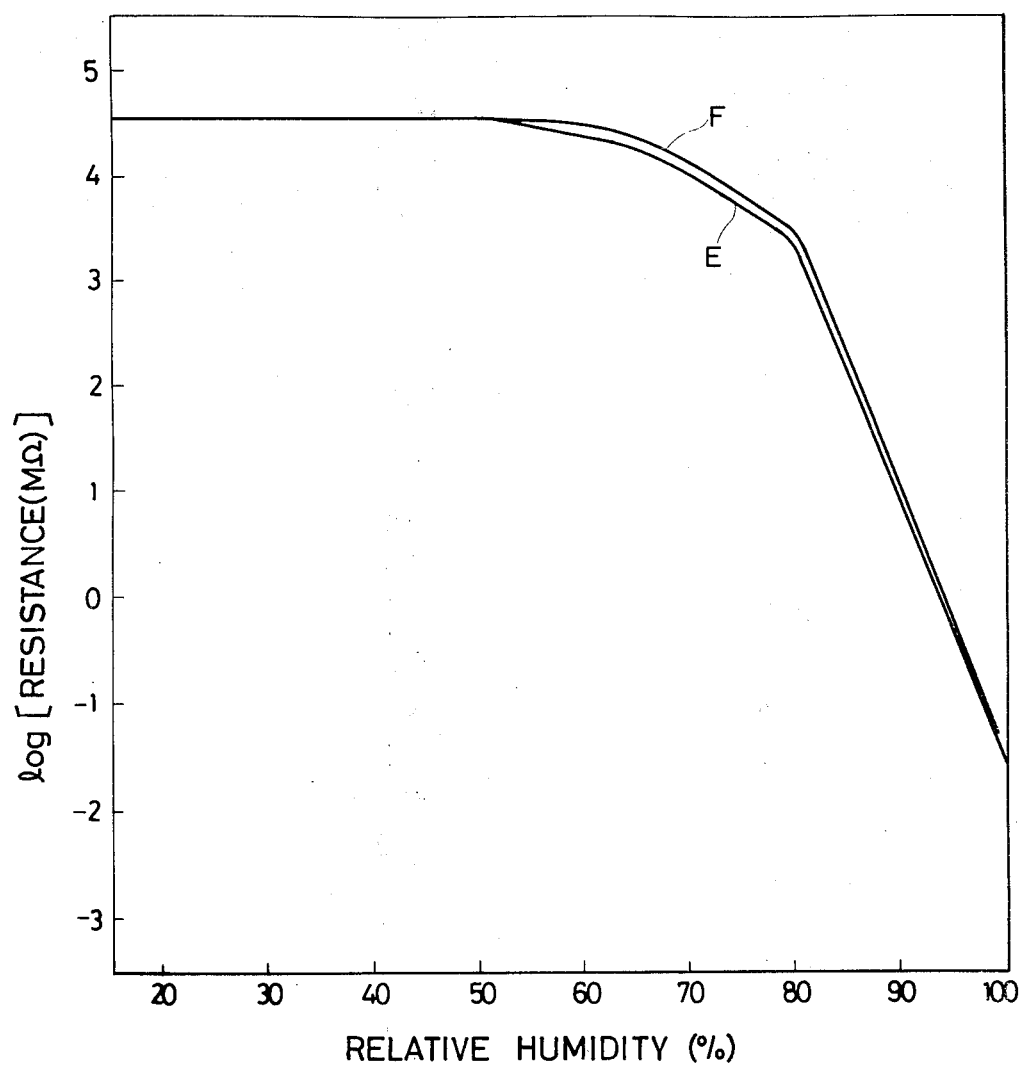
FIG. 12 is a graph showing a relative humidity-resistance characteristic and particularly showing a time dependent deterioration of the characteristic of the humidity sensitive device obtained by Example 4.

As seen from FIG. 12, the sample as exposed to the above described environmental condition (the curve E) and the sample as not exposed to such condition (the curve F) exhibit substantially the same relative humidity-resistance characteristics, which means that time dependent deterioration of the characteristic of the inventive device is of little problem in the practical use.

Although the above described experimentation was aimed to investigate time dependent deterioration of the characteristic of the inventive humidity sensitive device in a high humidity atmosphere, conversely another experimentation was made to investigate time dependent deterioration of the characteristic of the inventive humidity sensitive device in a dry atmosphere. More specifically, the inventive humidity sensitive device as supplied with 12 V of a direct current voltage is placed in a dry atmosphere at the temperature of 70° C. for 100 days. Then, as in case of the above described experimentation, the relative humidity-resistance characteristic is measured. Comparing the characteristic thus obtained with the characteristic of the humidity sensitive device as fabricated by the above described Example 4, it was observed that the difference therebetween is within the range of only a measurement error. The same has not been illustrated in a graph, however.

Although similar experimentation was made with respect to the humidity sensitive devices obtained by the other Examples 1 to 3 and 5 to 9, any time dependent deterioration of characteristics more than a measurement error was not observed.

Although the present invention has been described and illustrated in detail, it is clearly understood that the same is by way of illustration and example only and is not to be taken by way of limitation, the spirit and scope of the present invention being limited only by the terms of the appended claims.

What is claimed is:

1. A humidity sensitive device, comprising:

an insulating substrate having a major surface; first and second electrodes formed first and second electrodes formed on said major surface of said insulating substrate and spaced from each other;

first and second external connection terminals electrically coupled to and for external connection of said first and second electrodes respectively; and a humidity sensitive film formed on said major surface of said insulating substrate and covering at least the position of said major surface located between said electrodes, said humidity sensitive film comprising an inorganic polymer mainly including zirconium, and an organic polymer having compatibility with said inorganic polymer mainly including zirconium.

2. A humidity sensitive film in accordance with claim 1, wherein said humidity sensitive film further comprises a component for controlling the electrical resistance of said humidity sensitive film.

3. A humidity sensitive device in accordance with claim 2, wherein said resistance controlling component is at least one member selected from the group consisting of conductive powder, semiconductive powder and insulating powder.

4. A humidity sensitive device in accordance with claim 3, wherein said resistance controlling component comprises conductive powder.

5. A humidity sensitive device in accordance with claim 4, wherein said conductive powder is at least one member selected from the group consisting of carbon powder and palladium powder.

6. A humidity sensitive device in accordance with claim 3, wherein said resistance controlling component comprises semiconductive powder.

7. A humidity sensitive device in accordance with claim 6, wherein said semiconductive powder is powder of at least one member selected from the group consisting of $CrO_2$, $NiO$, $Fe_3O_4$, $ZnO$, $SnO_2$, $MnO_2$, $TiO_{2-x}$ ($0<x<2$), and semiconductive alkaline earths titanates.

8. A humidity sensitive device in accordance with claim 3, wherein said resistance controlling component comprises insulating powder.

9. A humidity sensitive device in accordance with claim 8, wherein said insulating powder comprises powder of at least one member selected from the group consisting of $TiO_2$, $ZrO_2$, $SiO_2$, and $Al_2O_3$.

10. A humidity sensitive device, comprising:

an insulating substrate having a major surface;

first and second electrodes formed on said major surface of said insulating substrate and spaced from each other;

first and second external connection terminals electrically coupled to and for external connection of said first and second electrodes respectively; and a humidity sensitive film formed on said major surface of said insulating substrate and covering at least the portion of said major surface located between said electrodes;

said humidity sensitive film comprising a coating disposed on said insulating substrate and covering at least the portion of said major surface located between said electrodes, said coating comprising a uniformly dispersed mixture comprising a zirconium compound and an organic polymer.

11. A humidity sensitive device in accordance with claim 10, wherein said uniformly dispersed mixture further comprises a component for controlling a resistance value.

12. A humidity sensitive device in accordance with claim 11, wherein said resistance controlling component is at least one member selected from the group consisting of conductive powder, semiconductive powder and insulating powder.

13. A humidity sensitive device in accordance with claim 12, wherein said resistance controlling component comprises conductive powder.

14. A humidity sensitive device in accordance with claim 13, wherein said conductive powder is at least one member selected from the group consisting of carbon powder and palladium powder.

15. A humidity sensitive device in accordance with claim 12, wherein said resistance controlling component comprises semiconductive powder.

16. A humidity sensitive device in accordance with claim 15, wherein said semiconductive powder is powder of at least one member selected from the group consisting of $CrO_2$, $NiO$, $Fe_3O_4$, $ZnO$, $SnO_2$, $MnO_2$, $TiO_{2-x}$ ($0<x<2$), and semiconductive alkaline earths titanates.

17. A humidity sensitive device in accordance with claim 12, wherein said resistance controlling component comprises insulating powder.

18. A humidity sensitive device in accordance with claim 17, wherein said insulating powder comprises powder of at least one member selected from the group consisting of $TiO_2$, $ZrO_2$, $SiO_2$, and $Al_2O_3$.

19. A humidity sensitive device in accordance with claim 10, wherein said zirconium compound is at least one member selected from the group consisting of zirconium oxychloride, zirconium acetate, zirconium chloride, zirconium bromide, zirconium hydroxide, zirconium iodide, zirconium nitrate, zirconium oxybromide, zirconium oxyiodide, zirconium sulfate, and those zirconium compounds denatured by hydration.

20. A humidity sensitive device in accordance with claim 10, wherein said organic polymer is a member having compatibility with said zirconium compound.

21. A humidity sensitive device in accordance with claim 20, wherein said organic polymer is a member selected from the group consisting of epoxy resin, silicone resin, and fluorine-contained polymers.

22. A humidity sensitive device in accordance with claim 20, wherein said organic polymer is at least one water soluble polymer selected from the group consisting of ethyl cellulose, methyl cellulose, carboxymethylcellulose, hydroxyigencellulose, polyethylene oxide and polyvinyl alcohol.

23. A method for manufacturing a humidity sensitive device, comprising the steps of:

preparing an insulating substrate having a major surface;

forming first and second electrodes on said major surface so as to be spaced apart from each other on said major surface;

providing first and second external connection terminals electrically coupled to and for external connection of said first and second electrodes, respectively;

preparing a uniformly dispersed mixture including a zirconium compound and an organic polymer;

coating said uniformly dispersed mixture on at least the portion of major surface of said insulating substrate located between said electrodes; and heating said uniformly dispersed mixture up to a temperature that does not decompose said organic polymer in said uniformly dispersed mixture as coated, whereby a humidity sensitive film is formed on said insulating substrate and between said electrodes.

24. A method for manufacturing a humidity sensitive device in accordance with claim 23, wherein said step of preparing said uniformly dispersed mixture comprises the step of admixing a resistance controlling component into said uniformly dispersed mixture for controlling the electrical resistance of said uniformly dispersed mixture.

25. A method for manufacturing a humidity sensitive device in accordance with claim 24, wherein said resistance controlling component is at least one member selected from the group consisting of conductive powder, semiconductive powder and insulating powder.

26. A method for manufacturing a humidity sensitive device in accordance with claim 25, wherein said resistance controlling component comprises conductive powder.

27. A method for manufacturing a humidity sensitive device in accordance with claim 26, wherein said conductive powder is at least one member selected from the group consisting of carbon powder and palladium powder.

28. A method for manufacturing a humidity sensitive device in accordance with claim 24, wherein said resistance controlling component comprises semiconductive powder.

29. A method for manufacturing a humidity sensitive device in accordance with claim 28, wherein said semiconductive powder is powder of at least one member selected from the group consisting of $CrO_2$, $NiO$, $Fe_3O_4$, $ZnO$, $SnO_2$, $MnO_2$, $TiO_{2-x}(0<x<2)$, and semiconductive alkaline earths titanates.

30. A method for manufacturing a humidity sensitive device in accordance with claim 25, wherein said resistance controlling component comprises insulating powder.

31. A method for manufacturing a humidity sensitive device in accordance with claim 30, wherein said insulating powder comprises powder of at least one member selected from the group consisting of $TiO_2$, $ZrO_2$, $SiO_2$, and $Al_2O_3$.

32. A method for manufacturing a humidity sensitive device in accordance with claim 23, wherein said zirconium compound is at least one member selected from the group consisting of zirconium oxychloride, zirconium acetate, zirconium chloride, zirconium bromide, zirconium hydroxide, zirconium iodide, zirconium nitrate, zirconium oxybromide, zirconium oxyiodide, zirconium sulfate, and those zirconium compounds denatured by hydration.

33. A method for manufacturing a humidity sensitive device in accordance with claim 23, wherein said organic polymer is a member having compatibility with said zirconium compound.

34. A method for manufacturing a humidity sensitive device in accordance with claim 33, wherein said organic polymer is a member selected from the group consisting of epoxy resin, silicone resin, and fluorine-contained polymers.

35. A method for manufacturing a humidity sensitive device in accordance with claim 33, wherein said organic polymer is at least one water soluble polymer selected from the group consisting of ethyl cellulose, methyl cellulose, carboxymethylcellulose, hydroxigencellulose, polyethylene oxide and polyvinyl alcohol.

* * * * *

UNITED STATES PATENT AND TRADEMARK OFFICE
CERTIFICATE OF CORRECTION

PATENT NO. : 4,263,576

DATED : April 21, 1981

INVENTOR(S) : Michihiro Murata et al

It is certified that error appears in the above-identified patent and that said Letters Patent are hereby corrected as shown below:

Column 2, line 22, for "metyl" read -- methyl --

Column 4, line 1, for "predetermind" read -- predetermined -- line 4, for "mixuture" read -- mixture --; and line 13, for "thereby" read -- thereto -- and for "past" read -- paste --

Column 6, line 55, for "2" read -- 1 --

Column 9, lines 1-2, delete "first and second electrodes formed"; line 41, for "semiconductive" read -- semiconductor --

Signed and Sealed this

Thirteenth Day of September 1983

[SEAL]

Attest:

GERALD J. MOSSINGHOFF

Attesting Officer

Commissioner of Patents and Trademarks